United States Patent [19]

Yardley et al.

[11] Patent Number: 5,486,518
[45] Date of Patent: Jan. 23, 1996

[54] 4-INDOLYLPIPERAZINYL DERIVATIVES

[75] Inventors: John P. Yardley, King of Prussia; Horace Fletcher, III, Pottstown, both of Pa.; Michael G. Kelly, Maidenhead; Alan C. White, Surrey, both of England

[73] Assignee: American Home Products Corporation, Madison, N.J.

[21] Appl. No.: 419,342

[22] Filed: Apr. 10, 1995

[51] Int. Cl.$^6$ .................... A61K 31/495; C07D 403/00
[52] U.S. Cl. ............................ 514/254; 544/373
[58] Field of Search ............... 544/373; 514/254

[56] References Cited

U.S. PATENT DOCUMENTS

| | | | |
|---|---|---|---|
| 4,988,814 | 1/1991 | Abou-Gharbia et al. | 544/295 |
| 5,340,812 | 8/1994 | Cliffe | 514/255 |

*Primary Examiner*—Cecilia Tsang
*Attorney, Agent, or Firm*—Richard K. Jackson

[57] ABSTRACT

This invention provides anxiolytic/antidepressant agents of the formula:

A compound of the formula:

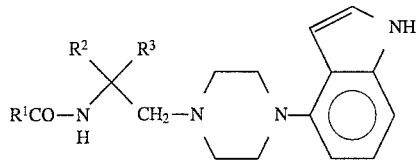

in which
$R^1$ is alkyl, cycloalkyl, aryl or arylalkyl;
$R^2$ is hydrogen or alkyl;
$R^3$ is phenyl, benzyl, substituted phenyl, or substituted benzyl in which the substituents are hydroxy, halo, alkoxy, trifluoromethyl, nitro, cyano, alkoxycarbonyl, amino or dialkylamino;
or a pharmaceutically acceptable salt thereof.

10 Claims, No Drawings

1

4-INDOLYLPIPERAZINYL DERIVATIVES

BACKGROUND OF THE INVENTION

U.S. Pat. No. 4,988,814 discloses a group of compounds in which the tertiary alkyl carboxylic acid acyl moiety appears. GB 2230781 discloses a group of 5-HT$_1$A antagonists which contain a heteroarylpiperazine moiety.

SUMMARY OF THE INVENTION

In accordance with this invention there is provided a group of novel compounds which exhibit serotonin 5HT$_1$A activity which characterizes them as compounds capable of regulating various physiological functions and behavior including anxiety and affective states. In addition, 5-HT$_1$-like antagonists, like those involved in the present disclosure have been shown to be useful in inhibiting the growth of certain cancers, such as human prostatic carcinoma. Hence, the compounds of this invention are useful in the treatment of cancer. The compounds of the invention are of the following structure:

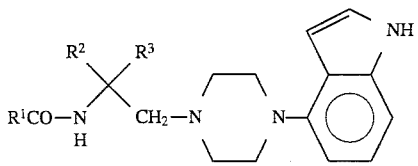

in which
  R$^1$ is alkyl of 1 to 6 carbon atoms, cycloalkyl of 5 to 7 carbon atoms, aryl of 6 to 10 carbon atoms or arylalkyl of 7 to 12 carbon atoms;
  R$^2$ is hydrogen or alkyl of 1 to 6 carbon atoms;
  R$^3$ is phenyl, benzyl, substituted phenyl, or substituted benzyl in which the substituents are hydroxy, halo, alkoxy of 1 to 6 carbon atoms, trifluoromethyl, nitro, cyano, alkoxycarbonyl of 2 to 7 carbon atoms, amino or dialkylamino in which each alkyl group contains 1 to 6 carbon atoms;
  or a pharmaceutically acceptable salt thereof.

The halogen substituent referred to above may be chlorine, bromine, fluorine or iodine, fluorine being preferred. The pharmaceutically acceptable salts are derived from known inorganic or organic acids such as hydrochloric, hydrobromic, sulfuric, nitric, phosphoric, methanesulfonic, ethanesulfonic, hydroxyethanesulfonic, toluene sulfonic, naphthalenesulfonic, formic, acetic, propionic, oxalic, succinic, glycollic, lactic, malic, tartaric, citric, ascorbic, maleic, hydroxymaleic, pyruvic, phenylacetic, benzoic, para-amino benzoic, para-hydroxybenzoic, salicylic, sulfanilic acids, and the like.

The compounds of this invention contain a chiral center, providing for various stereoisomeric forms of the compounds such as racemic mixtures as well as the individual optical isomers, which isomers can be either prepared directly by asymmetric or stereospecific synthesis or by conventional separation of epimers or optical isomers from the racemic mixture.

The preferred compounds are those of the (R) configuration in which R$^1$ is phenyl or cyclohexyl, R$^2$ is hydrogen and R$^3$ is phenyl or benzyl, or a pharmaceutically acceptable salt thereof.

The compounds of this invention (G) are prepared by a sequence beginning with the reaction of 4-indolyl-piperazine (B) with an N-protected aminoacid (A) in the presence of a coupling reagent such as 1,1'-carbonyldiimidazole, iso-butylchloroformate, diethylcyanophosphonate or a carbodiimide, to give the N-protected aminoacid amide (C). The protecting group R$^4$ for the aminoacid is of the urethane type, particularly useful are those in which R$^4$ is tertiary-butyloxycarbonyl (removable by acid) or benzyloxycarbonyl (removable by hydrogenation or by HBr).

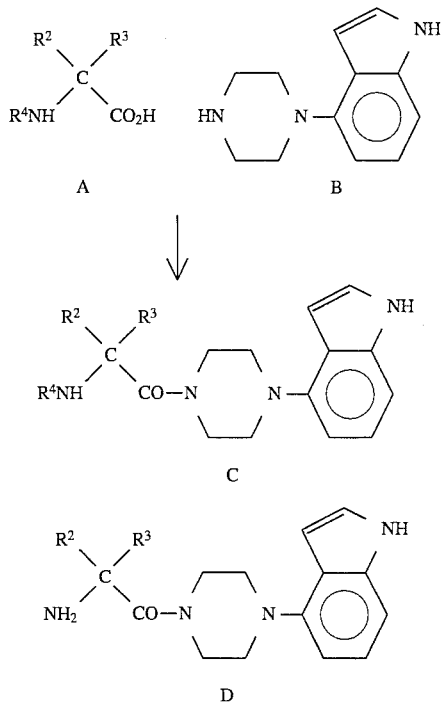

After deprotection of (C) the aminoacid amide may be reduced to (E) using either diborane or LiAlH$_4$.

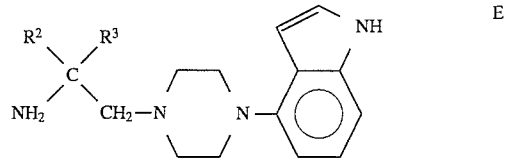

Acylation with a carboxylic acid (F) affords the compounds (G) of the invention.

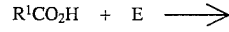

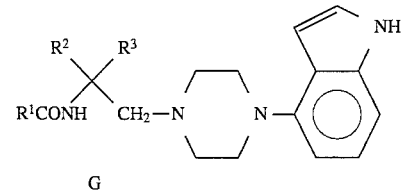

Examples of acylating reactants include the acid halides (e.g. acid chlorides), azides, anhydrides, imidazolides (e.g. obtained from carbonyldiimidazole) or o-acylureas (e.g. obtained from a carbodiimide).

The compounds of this invention possess high affinity for the serotonin 5-HT$_1$A receptor, and consequently, they are useful as antidepressant and anxiolytic agents for the treatment of a variety of central nervous system disorders such as depression, anxiety, sleep disorders, sexual dysfunction, alcohol and cocaine addiction, cognition enhancement and related problems. In addition, the compounds of this invention show marked selectivity for the 5-HT$_1$A receptors as opposed to the α1 receptors.

High affinity for the serotonin 5-HT$_1$A receptor was established by testing the claimed compound's ability to displace [$^3$H]8-OHDPAT (dipropylaminotetralin) from the 5-HT$_1$A serotonin receptors in rat hippocampal membrane homogenate following the procedure of B. S. Alexander and M. D. Wood, J. Pharm. Pharmacol. 1988, 40, 888–891. The compound of Example 1 exhibited an IC$_{50}$ of 2 nM; the compound of Example 2 exhibited an IC$_{50}$ binding potency of 35.5 nM; the product of Example 3 exhibited an IC$_{50}$ of 5 nM and the product of Example 4 exhibited an IC50 of 8.3 nM. These compounds are highly selective for the 5-HT$_1$A receptors in comparison with their affinity for other receptors such as the alpha 1, alpha 2, D 1, etc. receptors.

Based upon this receptor binding data, the compounds of this invention are characterized as anxiolytic and/or antidepressant agents useful in the treatment of depression and in alleviating anxiety. As such, the compounds may be administered neat or with a pharmaceutical carder to a patient in need thereof. The pharmaceutical carder may be solid or liquid.

Applicable solid carriers can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carder having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or phamaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carder can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form. Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific patient suffering from depression or anxiety must be subjectively determined by the attending physician. The variables involved include the specific state of anxiety or depression, and the size, age and response pattern of the patient.

The following examples are presented, without limitation on the scope of the invention claimed hereinafter, to illustrate the preparation of representative members of the compounds of the invention.

EXAMPLE 1

(R)-Cyclohexanecarboxylic acid-(2-[4-indolyl]-1-piperazin-1-yl]-1-phenyl-ethyl)-amide Benzyloxycarbonyl-D-phenylglycine (2.36 g, 0.0083 tool), and N-methylmorpholine (0.84 g, 0.0083 mol) were stirred in 100 mL of methylene chloride at −15° C. under a nitrogen atmosphere as isobutylchloroformate (1.13 g, 0.0083 mol) was added. After 15 minutes, 4-piperazinylindole (1.33 g, 0.0075 mol) was added and the mixture was stirred as it reached room temperature over 20 hours. The solution was washed with water (2×), saturated NaHCO$_3$ (2×) and dried over anhydrous Na$_2$SO$_4$. Evaporation of solvent left 3.6 g of product as a gum which was stirred in 30% HBr in acetic acid (100 mL) at room temperature for 30 minutes. Diethyl ether (300 mL) was added and the hydrobromide salt was filtered, washed with diethyl ether, and dried in vacuo overnight. The salt was shaken in 1N NaOH and the amine was extracted with methylene chloride (3×). The extracts were washed with water, dried over anhydrous Na$_2$SO$_4$, and evaporated to a gum, yield 1.6 g (57.6% from cbz-D-phenylglycine).

(R)(1-Phenylglycyl)-4-(4-indolyl)piperazine (1.6 g, 4.92 mmol) and lithium aluminum hydride (0.81 g, 21.7 mmol) were refluxed in THF (500 mL) overnight under nitrogen. The cooled reaction was quenched with 1N NaOH (4.92 mL), stirred for 30 minutes, filtered, and the filtrate was evaporated. The residue was dissolved in ethyl acetate, washed with water, then brine, and dried (Na$_2$SO$_4$). Evaporation of the solvent left (R)-2-(4-indolyl)-piperazin- 1-yl-1-phenyl-ethylamine (1.39 g). Yield 88%. The IR spectrum was devoid of carbonyl peaks. Mass spectrum, EI M+.M/H 320.

(R)-2-[4-(1H-Indol-4-yl)piperazin- 1-yl]- 1-phenyl-ethylamine (1.8 g, 5.5 mmol), cyclohexanecarbonyl chloride (0.8 g, 5.5 mmol) and diisopropyl ethylamine (1 mL, 5.5 mmol) were stirred in THF (50 mL) in an ice bath and allowed to reach room temperature overnight. The solvent was evaporated and the residue was shaken with ethyl acetate and water. The organic layer was washed with saturated NaHCO$_3$, then brine and dried (Na$_2$SO$_4$). After removal of solvent the product was purified on a silica dry column (400 mL) and eluted with 1:1 ethyl acetate/hexane. Yield 1.4 g (59%). The product was dissolved in ethyl acetate containing 10% ethanol, acidified with 3.6N HCl in ethyl acetate, diluted with two volumes of diethyl ether and filtered. The salt was washed with diethyl ether and dried in vacuo overnight at room temperature to provide the title compound as the hydrochloride, 2.5 hydrate. Yield 1.3 g (46.2%). MP 210°–215° C.; IR 1650 cm$^{-1}$. Mass spectrum EI M$^+$430. $^1$H NMR (DMSO-d$_6$): δ1.2–1.4 (m, 6H), 1.58–1.62 (d, 1H), 1.62-1.8 (m, 4H), 1.8–1.88 (d,1H), 2.28–2.38 (m, 1H), 3.65–3.75 (t, 2H), 3.85–4.05 (s, 1H), 6.45 6.55–6.58 (d,1H), 6.95–7.0 (t,1H), 7.05–7.14 (d, 1H), 7.25–7.3 (t, 2H), 6.35–7.24 (m,5H). [α]$_D^{25}$ –28.8 c=1.00 EtOH.

Analytical: C$_{27}$ H$_{34}$N$_4$ O.HCl.2.5 H$_2$ O Calc'd: C, 63.53; H, 7.87; N, 10.94 Found: C, 63.46; H, 7.43; N, 10.87

EXAMPLE 2

(R)-Acetic acid (2-[4-indolyl]-1-piperazin-1-yl]-1-phenyl-ethyl)-amide (R)-2-[4-1H-indolyl-4-yl)-piperazin 1-yl]- 1-phenyl-ethylamine (0.5 g, 1.5 mmol), acetic anhydride (0.237 g, 2.35 mmol) and triethylamine (0.24 g, 2.35 mmol) were stirred in methanol (50 mL) overnight. The methanol was evaporated and the residue was shaken with dichloromethane and water, then saturated NaHCO$_3$. The organic solution was dried (Na$_2$SO$_4$) and evaporated. Yield 0.5 g (92%). The amine was dissolved in dichloromethane (15 mL), acidified with 3.6N HCl in ethyl acetate, filtered, and dried in vacuo at room temperature to provide the title compound as the hydrochloride, sesquihydrate. Yield 0.42 g (72%). MP 188°–190° C.; IR 1650 cm$^{-1}$. Mass spectrum EI M+362. $^1$H NMR (DMSO-d$_6$): δ1.97 (s, 3H),3.2–3.8 (m, 10H), 5.38–5.42 (m, 1H), 6.45 (S, 1H), 6.55–6.7 (d, 1H), 6.97–7.02 (t, 1H), 7.1–7.13 (m, 1H), 7.18–7.25 (m, 2H), 7.35–7.42 (6, 2H), 7.43–7.46 (d, 2H), 8.78–8.90 d, 1H), 10.56–10.67 (s 1H),11.17 (s,1H), [α]$_D^{25}$36.8, c=1.01 ethanol.

Analytical: C$_{22}$ H$_{26}$N$_4$ O.HCl. 1.5 H$_2$ O Calc'd: C, 57.15; H, 6.76; N, 12.11 Found: C, 57.44; H, 6.77; N, 11.82

EXAMPLE 3

(R)-Benzoic acid-(2-[4-indolyl]1-piperazin-1-yl]1-phenyl-ethyl)-amide (R)-2-[4-(1 H-Indol4-yl)-piperazin-1-yl]- 1-phenyl-ethylamine (0.5 g, 1.5 mmol), diisopropylethylamine (0.22 g, 1.7 mmol) and benzoylchloride (0.239 g, 1.7 mmol) were stirred in dichloromethane (50 mL) overnight at room temperature. The solution was washed with water, saturated NaHCO$_3$, dried (Na$_2$SO$_4$) and evaporated. Yield 0.625 g (98.2%). The hydrochloride salt was prepared in ethyl acetate with 3.6 N HCl in ethyl acetate and dilution with diethyl ether. The product was filtered, washed with diethyl ether and dried in vacuo overnight. Yield 0.26 g (34.3%); MP 178°–180° C., IR 1650 cm$^-$1. Mass spectrum EI M$^+$424.$^1$H NMR (DMSO-d$_6$): δ3.14–3.25 (m, 2H), 3.4–3.58 (m, 2H), 3.59–3.65 (t, 2H), 3.65–3.85 (m, 4H), 5.62–5.7 (t, 1H), 6.4–6.55 (d, 1H), 6.95–7.0 (t, 1H), 7.06–7.10 (d, 1H), 7.26–7.3 (t, 1H), 7.3–7.35 (d, 1H), 7.35–7.4 (t, 2H), 7.45–7.6 (m, 5H), 8.0–8.06 (d, 2H), 9.3–9.38 (d, 1H), 10.48–10.6 (s, 1H), 11.12–11.16 (s, 1H). [α]$_D^{25}$–19.99, c=1.00 ethanol.

Analytical: C$_{27}$ H$_{28}$N$_4$ O.HCl.0.5 H$_2$0 Calc'd: C, 64.02; H, 6.17; N, 11.06 Found: C, 63.99; H, 6.37; N, 10.63

EXAMPLE 4

(R)- Cyclohexane Carboxylic Acid 1-Phenylmethyl -2-[1-[4-(4-indolyl) piperazinyl]] ethylamide A tetrahydrofuran solution (40 mL) of N-t-Boc-D-Phe (4.9 g) was stirred under argon and treated portionwise with carbonyldiimidazole (CDI)( 1.1 equivalents, 3.3 g). After stirring for 15 minutes at ambient temperature, the indolylpiperazine (3.7 g, 1 equivalent) was added and the reaction mixture stirred for 16 hours. The solvent was removed in vacuo, water (100 mL) added and the product extracted into ethyl acetate (3×100 mL). The organics were dried (Na$_2$SO$_4$) and concentrated in vacuo to give 8.9 g of (R)-4-[4-(1H-indolyl)]-1-[2-N-(tertiary butoxycarbonyl)amino-3-phenyl] propionyl piperazine. The product was purified by chromatography on neutral alumina to give a white solid. (5.2 g, 63% yield) mp=102° C.

Elemental analysis for C$_{26}$H$_{32}$N$_4$O$_3$ 0.25 H$_2$ O Calc'd: C, 68.93; H, 7.23; N, 12.37 Found: C, 69.01; H, 7.39; N, 12.18

A dichloromethane solution (20 mL) of the amide (3.4 g) produced in the previous paragraph was treated with trifluoroacetic acid (10 mL) under argon. After stirring for one hour, the solvent was removed in vacuo. Water (100 mL) was added and the solution was neutralized to pH 7 with aqueous NaHCO3 solution. The product was extracted into ethyl acetate (3×100 mL). The organics were dried (Na$_2$SO$_4$) and concentrated to give 2.56 g of (R)-4-[4-(1H-indolyl)]-1-[2-amino-3-phenyl] propionyl piperazine as the trifluoroacetate salt. (97% yield) mp=91° C.

Elemental analysis for C$_{21}$H$_{24}$N$_4$O.CF$_3$CO$_2$H Calc'd: C, 59.73; H, 5.45; N, 12.11 Found: C, 60.53; H, 5.95; N, 11.63

Lithium aluminum hydride (0.78 g) was added portionwise to a stirred solution of the amide (2.4 g) in tetrahydrofuran (30 mL) at ambient temperature. The mixture was refluxed for 15 minutes to complete the reaction. Upon cooling to ambient temperature, the excess hydride was destroyed by adding saturated ammonium chloride solution cautiously. The product was extracted into ethyl acetate (3×100 mL), dried over sodium sulphate, and concentrated in vacuo to give 2.13 g of crude (R)-4-[4-(1H-indolyl)]-1-[ 2-amino-3-phenyl] propyl piperazine, which was used directly in the next step.

Triethylamine (1.29 g, 2 equivalents) was added to a dichloromethane solution (20 mL) of the crude amine (2.13 g, 1 equivalent) at 0° C. under argon and the stirred solution was treated with cyclohexanoyl chloride (1.03 g, 1.1 equivalents). After 3 hours, the solvent was removed in vacuo, water (100 mL) was added and the pH was made basic with aqueous 1N NaOH. The product was extracted into ethyl acetate ( 3×100 mL), dried over sodium sulphate and concentrated to give 3 g of crude product. The crude product was purified by chromatography over silica gel to afford pure (R)-cyclohexane carboxylic acid 1-phenylmethyl -2-[ 1-[4-(4indolyl)piperazinyl]] ethylamide as a white solid. The monohydrochloride was obtained as a cream colored solid. mp=142° C.

Elemental analysis for C$_{28}$H$_{36}$N$_4$O.HCl.H$_2$O Calc'd: C, 67.38; H, 7.88; N, 11.23 Found: C, 67.67; H, 7.71; N, 11.09

What is claimed is:
1. A compound of the formula:

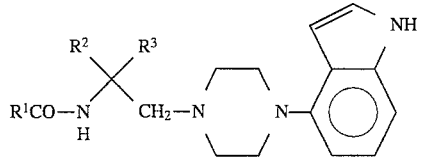

in which
R$^1$ is alkyl of 1 to 6 carbon atoms, cycloalkyl of 5 to 7 carbon atoms, aryl of 6 to 10 carbon atoms or arylalkyl of 7 to 12 carbon atoms;
R$^2$ is hydrogen or alkyl of 1 to 6 carbon atoms;
R$^3$ is phenyl, benzyl, substituted phenyl, or substituted benzyl in which the substituents are hydroxy, halo, alkoxy of 1 to 6 carbon atoms, trifluoromethyl, nitro, cyano, alkoxycarbonyl of 2 to 7 carbon atoms, amino or dialkylamino, each alkyl group having 1 to 6 carbon atoms;

or a pharmaceutically acceptable salt thereof.

2. A compound of claim 1, of the (R) configuration in which $R^1$ is phenyl or cyclohexyl, $R^2$ is hydrogen and $R^3$ is phenyl or benzyl, or a pharmaceutically acceptable salt thereof.

3. A compound of claim 1 which is cyclohexanecarboxylic acid-(2-[ 4-indolyl]-1-yl]-1-phenyl-ethyl)amide or a pharmaceutically acceptable salt thereof.

4. The compound of claim 1 which is (R)-cyclohexanecarboxylic acid-(2-[4-[4-indolyl]-1-piperazin-1-yl]-1-phenyl-ethyl)-amide or a pharmaceutically acceptable salt thereof.

5. The compound of claim 1 which is acetic acid (2-[4-indolyl]-1-piperazin- 1-yl-]-1-phenyl-ethyl)-amide or a pharmaceutically acceptable salt thereof.

6. A compound of claim 1 which is (R)-acetic acid (2-[4-indolyl]-1-piperazin-1-yl]-1 -phenyl-ethyl)-amide or a pharmaceutically acceptable salt thereof.

7. The compound of claim 1 which is benzoic acid-(2-[4-indolyl]-1-piperazin- 1-yl]-1-phenyl-ethyl)-amide or a pharmaceutically acceptable salt thereof.

8. The compound of claim 1 which is (R)-benzoic acid-(2-[4-indolyl]-1-piperazin-1-yl]- 1-phenyl-ethyl)-amide or a pharmaceutically acceptable salt thereof.

9. The compound of claim 1 which is cyclohexane carboxylic acid 1-phenylmethyl-2-[1-[4-( 4-indolyl)piperazinyl]]ethylamide or a pharmaceutically acceptable salt thereof.

10. The compound of claim 1 which is (R)-cyclohexane carboxylic acid 1-phenylmethyl- 2-[1-[4-(4-indolyl)piperazinyl]]ethylamide or a pharmaceutically acceptable salt thereof.

\* \* \* \* \*